(12) United States Patent
Wang et al.

(10) Patent No.: US 11,701,405 B2
(45) Date of Patent: Jul. 18, 2023

(54) CHIMERIC ANTIGEN RECEPTORS AND METHODS FOR REDUCING TOXICITY

(71) Applicant: City of Hope, Duarte, CA (US)

(72) Inventors: Xiuli Wang, Temple City, CA (US); Stephen J. Forman, Duarte, CA (US); Lawrence Stern, Duarte, CA (US); Christine E. Brown, Duarte, CA (US); Joseph Cohen, Duarte, CA (US)

(73) Assignee: City of Hope, Duarte, CA (US)

( * ) Notice: Subject to any disclaimer, the term of this patent is extended or adjusted under 35 U.S.C. 154(b) by 398 days.

(21) Appl. No.: 16/964,471

(22) PCT Filed: Jan. 25, 2019

(86) PCT No.: PCT/US2019/015252
§ 371 (c)(1),
(2) Date: Jul. 23, 2020

(87) PCT Pub. No.: WO2019/148006
PCT Pub. Date: Aug. 1, 2019

(65) Prior Publication Data
US 2021/0046155 A1 Feb. 18, 2021

Related U.S. Application Data

(60) Provisional application No. 62/622,583, filed on Jan. 26, 2018.

(51) Int. Cl.
*A61K 38/17* (2006.01)
*A61K 35/17* (2015.01)
(Continued)

(52) U.S. Cl.
CPC ............ *A61K 38/177* (2013.01); *A61K 35/17* (2013.01); *C07K 16/18* (2013.01); *C12N 15/86* (2013.01); *C07K 2317/622* (2013.01)

(58) Field of Classification Search
CPC .......... C07K 2317/622; C07K 16/2884; C07K 16/18; A61K 38/177; A61K 35/17; C12N 15/86
See application file for complete search history.

(56) References Cited

FOREIGN PATENT DOCUMENTS

WO WO 2016/210447 12/2016
WO WO-2016210447 A1 * 12/2016 .............. A61P 35/00

OTHER PUBLICATIONS

Stoiber S, Cadilha BL, Benmebarek MR, Lesch S, Endres S, Kobold S. Limitations in the Design of Chimeric Antigen Receptors for Cancer Therapy. Cells. May 17, 2019;8(5):472. doi: 10.3390/cells8050472. PMID: 31108883; PMCID: PMC6562702. (Year: 2019).*

(Continued)

*Primary Examiner* — Adam Weidner
*Assistant Examiner* — Laura Ann Essex
(74) *Attorney, Agent, or Firm* — Fish & Richardson P.C.

(57) ABSTRACT

Nucleic acid molecules that include a nucleotide sequence encoding a chimeric antigen receptor (CAR) and a nucleotide sequence encoding a protease sensitive scFv, wherein the chimeric antigen receptor comprises: an scFv targeting a tumor antigen, a spacer, a transmembrane domain, a co-stimulatory domain, and a CD3ζ signaling domain; and the protease-sensitive scFv and the scFv target the same tumor antigen are described.

7 Claims, 10 Drawing Sheets

Specification includes a Sequence Listing.

A

B

(51) Int. Cl.
  *C07K 16/18* (2006.01)
  *C12N 15/86* (2006.01)

(56) References Cited

OTHER PUBLICATIONS

Kortt AA, Dolezal O, Power BE, Hudson PJ. Dimeric and trimeric antibodies: high avidity scFvs for cancer targeting. Biomol Eng. Oct. 15, 2001;18(3):95-108. doi: 10.1016/s1389-0344(01)00090-9. PMID: 11566601. (Year: 2001).*

Casucci et al., "CD44v6-targeted T cells mediate potent antitumor effects against acute myeloid leukemia and multiple myeloma," Blood, Nov. 14, 2013, 122(20):3461-72.

Casucci et al., "Co-expression of a suicide gene in CAR-redirected T cells enables the safe targeting of CD44v6 for leukemia and myeloma eradication," Blood, American Society of Hematology, Dec. 1, 2012, 120(21).

Choi et al., "EpiSweep: Computationally driven reengineering of therapeutic proteins to reduce immunogenicity while maintaining function," Methods in Molecular Biology, Jan. 1, 2018, 1529:375-398.

Database: Geneseq [Online], "Anti-CD44v6 Ab VH region, SEQ:20," retrieved from EBI accession No. GSP:BDV09672, Jun. 1, 2017, Database accession No. BDV09672; & WO 2017/055392 (Hoffman-La Roche), Apr. 6, 2017, 1 page.

Gai et al., "Yeast surface display for protein engineering and characterization," Current Opinion in Structural Biology, Aug. 1, 2007, 17(4):467-73.

Jaspers et al., "Development of CAR T cells designed to improve antitumor efficacy and safety," Pharmacology & Therapeutics, Oct. 1, 2017, 178:83-91.

PCT International Preliminary Report on Patentability in International Appln. No. PCT/US2019/015252, dated Jul. 28, 2020, 8 pages.

PCT International Search Report and Written Opinion in International Appln. No. PCT/US2019/015252, dated Jun. 17, 2019, 12 pages.

Prudova et al., "Multiplex N-terminome analysis of MMP-2 and MMP-9 substrate degradomes by iTRAQ-TAILS quantitative proteomics," Molecular & Cellular Proteomics, May 1, 2010, 9(5):894-911.

Tillotson et al., "Antibody affinity maturation using yeast display with detergent-solubilized membrane proteins as antigen sources," Protein Engineering, Design & Selection, Feb. 1, 2013, 26(2):101-12.

Wang et al., "A transgene-encoded cell surface polypeptide for selection, in vivo tracking, and ablation of engineered cells," Blood, Aug. 4, 2011, 118(5):1255-63.

Wang et al., "Engraftment of human central memory-derived effector CD8+ T cells in immunodeficient mice," Blood, The Journal of the American Society of Hematology, Feb. 10, 2011, 117(6):1888-98.

Zaccolo et al., "An approach to random mutagenesis of DNA using mixtures of triphosphate derivatives of nucleoside analogues," Journal of Molecular Biology, Feb. 2, 1996, 255(4):589-603.

* cited by examiner

A

B

A

B

CD44scFv-IgG4(L235E)-CD4tm-41BB-Zeta-T2A-EGFRt

<u>MLLLVTSLLLCELPHPAFLLIP</u><u>EVQLVESGGGLVKPGGSLRLSCAASGFTFSSYDMSWVRQAPGKGLEWVSTI</u>
<u>GMCSFRa signal peptide</u>     CD44v6 scFv <u>SSGGSYTYYLDSIKGRFTISRDNAKNSLYLQMNSLRAEDTAVYYCARQGLDYWGRGTLVTVSSGGGGSGGG</u>

<u>GSGGGGSEIVLTQSPATLSLSPGERATLSCSASSSINYIYWYQQKPGQAPRLLIYLTSNLASGVPARFSGSGSG</u>

<u>TDFTLTISSLEPEDFAVYYCLQWSSNPLTFGGGTKVEIK</u><u>ESKYGPPCPPCPAPEFEGGPSVFLFPPKPKDTLMIS</u>
                                                    IgG4(SmP)(L235E)

<u>RTPEVTCVVVDVSQEDPEVQFNWYVDGVEVHNAKTKPREEQFNSTYRVVSVLTVLHQDWLNGKEYKCKV</u>

<u>SNKGLPSSIEKTISKAKGQPREPQVYTLPPSQEEMTKNQVSLTCLVKGFYPSDIAVEWESNGQPENNYKTTP</u>

<u>PVLDSDGSFFLYSRLTVDKSRWQEGNVFSCSVMHEALHNHYTQKSLSLSLGK</u><u>MALIVLGGVAGLLLFIGLGIF</u>
                                                         CD4 transmembrane <u>FKRGRKKLLYIFKQPFMRPVQTTQEEDGCSCRFPEEEEGGCEL</u><u>GGGRVKFSRSADAPAYQQGQNQLYNELN</u>
 4-1BB cyto                                  CD3 zeta <u>LGRREEYDVLDKRRGRDPEMGGKPRRKNPQEGLYNELQKDKMAEAYSEIGMKGERRRGKGHDGLYQGLS</u>

<u>TATKDTYDALHMQALPPR</u><u>LEGGGEGRGSLLTCGDVEENPGPR</u> <u>MLLLVTSLLLCELPHPAFLLIP</u><u>RKVCNGIGI</u>
                         T2A                                        EGFRt

<u>GEFKDSLSINATNIKHFKNCTSISGDLHILPVAFRGDSFTHTPPLDPQELDILKTVKEITGFLLIQAWPENRTDLH</u>

<u>AFENLEIIRGRTKQHGQFSLAVVSLNITSLGLRSLKEISDGDVIISGNKNLCYANTINWKKLFGTSGQKTKIISNR</u>

<u>GENSCKATGQVCHALCSPEGCWGPEPRDCVSCRNVSRGRECVDKCNLLEGEPREFVENSECIQCHPECLPQ</u>

<u>AMNITCTGRGPDNCIQCAHYIDGPHCVKTCPAGVMGENNTLVWKYADAGHVCHLCHPNCTYGCTGPGLE</u>

<u>GCPTNGPKIPSIATGMVGALLLLLVVALGIGLFM</u>

EVQLVESGGGLVKPGGSLRLSCAASGFTFSSYDMSWVRQAPGKGLEWVSTISSGGSYTYYLDSIKGRFTISR
DNAKNSLYLQMNSLRAEDTAVYYCARQGLDYWGRGTLVTVSSGSTSGSKGPLGLAGATKGSEIVLTQSPATLSL
SPGERATLSCSASSSINYIYWYQQKPGQAPRLLIYLTSNLASGVPARFSGSGSGTDFTLTISSLEPEDFAVYYCL
QWSSNPLTFGGGTKVEIK

B

EVQLVESGGGLVKPGGSLRLSCAASGFTFSSYDMSWVRQAPGKGLEWVSTISSGGSYTYYLDSIKGRFTISR
DNAKNSLYLQMNSLRAEDTAVYYCARQGLDYWGRGTLVTVSSGSTSGSKGPKGLKGATKGSEIVLTQSPATLSL
SPGERATLSCSASSSINYIYWYQQKPGQAPRLLIYLTSNLASGVPARFSGSGSGTDFTLTISSLEPEDFAVYYCL
QWSSNPLTFGGGTKVEIK

C

EVQLVESGGGLVKPGGSLRLSCAASGFTFSSYDMSWVRQAPGKGLEWVSTISSGGSYTYYLDSIKGRFTISR
DNAKNSLYLQMNSLRAEDTAVYYCARQGLDYWGRGTLVTVSS

D

SEIVLTQSPATLSLSPGERATLSCSASSSINYIYWYQQKPGQAPRLLIYLTSNLASGVPARFSGSGSGTDFTLTIS
SLEPEDFAVYYCLQWSSNPLTFGGGTKVEIK

FIGURE 10

CHIMERIC ANTIGEN RECEPTORS AND METHODS FOR REDUCING TOXICITY

CLAIM OF PRIORITY

This application is a U.S. National Phase Application under 35 U.S.C. § 371 of International Application No. PCT/US2019/015252, filed on Jan. 25, 2019, which claims the benefit of U.S. Provisional Application Ser. No. 62/622, 583, filed on Jan. 26, 2018. The entire contents of the foregoing are incorporated herein by reference.

SEQUENCE LISTING

This application contains a Sequence Listing that has been submitted electronically as an ASCII text file named 40056-0039US1_ST25.txt. The ASCII text file, created on Jan. 31, 2023, is 50,858 bytes in size. The material in the ASCII text file is hereby incorporated by reference in its entirety.

BACKGROUND

Cancer initiating/stem cells (CSCs) (also known as tumor stem cells [TSCs]) are a distinct and highly motile and aggressive subpopulation of cells that reside within tumors, with the capacity to proliferate, differentiate and seed tumors1. Initially identified in acute myeloid leukemia (AML), CSCs have also been identified in solid tumors. TSCs are resistant to radio/chemotherapy and evidence suggests that they may be responsible for disease relapse. Complete elimination and prevention of tumor recurrence and growth relies on the eradication of CSCs, which remains challenging for the treatment of cancers, including hematopoietic malignancies. The CD44 transmembrane receptor is a cell adhesion glycoprotein that binds to components of the extracellular matrix (ECM) such as osteopontin, hyaluronan, collagen, laminin and fibronectin. CD44 has many biological functions including cellular growth, survival, and differentiation. Evidence also suggests that it is involved in tumor migration and metastasis. CD44 is widely expressed in a variety of cancers, and is a biomarker for CSCs. A splice variant of CD44, CD44 variant 6 (CD44v6), is overexpressed on malignant hematopoietic cells including AML, B cell malignancies and multiple myeloma (MM), especially in late stage diseases. CD44v6 plays an important role in proliferation, homing, and metastasis of tumor stem cells.

While CD44v6 appears to be an excellent target for CAR T cell therapy, its expression in human keratincytes and other tissues, as well as in monocytes, presents a challenge to CAR T cell or targeted antibody mediated therapy due to on-target off-tumor toxicity. Previous efforts using antibody drug conjugates employing bivatuzumab (a CD44v6 specific antibody) resulted in skin toxicity and fatalities from toxicity related events. To address on-target off-tumor toxicity, Casucci and colleagues offer the first preclinical studies using CAR-T cells that incorporate a suicide gene to target CD44v6 in AML and MM.

SUMMARY

Described herein is a nucleic acid molecule comprising a nucleotide sequence encoding a chimeric antigen receptor (CAR) and a nucleotide sequence encoding a protease sensitive scFv, wherein the chimeric antigen receptor comprises: an scFv targeting a tumor antigen, a spacer, a transmembrane domain, a co-stimulatory domain, and a CD3ζ signaling domain; and the protease-sensitive scFv and the scFv target the same tumor antigen. In some cases, the scFv within the CAR has VH and VL sequences that are identical to that of the protease sensitive CAR. The protease sensitive CAR further include a protease sensitive amino acid sequence (e.g., an MMP-2 or MMP-9 sensitive amino acid sequence) between the VH and VL sequences.

Described herein are methods for using CD44v6 targeted CAR T cells to treat a variety of cancers while reducing on-target, off-tumor toxicity. The methods entail the use of CD44v6 CAR T cells that secrete a soluble, protease-susceptible CD44v6 scFv that can block CAR binding in healthy tissue, but will be cleaved by cancer-specific proteases (e.g., MMP-2 or MMP-9) in the tumor site, allowing for CAR T cell binding and activation. Thus, described herein is a population of T cells expressing both a CD44v6-targeted CAR and a protease sensitive CD44v6 scFv.

In various embodiments: the protease sensitive scFv is sensitive to MMP-2 or MMP-9; the protease sensitive scFv comprises a $V_H$ domain and a $V_L$ domain joined by a protease-sensitive linker; the scFv and the protease-sensitive scFv have the same CDR sequences; the nucleic acid molecule comprises a nucleotide sequence encoding a T2A skip sequence; the nucleotide sequence encoding a T2A skip sequence is located between the nucleotide sequence encoding the chimeric antigen receptor and the nucleotide sequence encoding a protease sensitive; the tumor antigen is CD44v6; the scFv comprises the amino acid sequence of SEQ ID NO:1; and the $V_H$ domain of the protease sensitive scFv comprises SEQ ID NO: 33 and the $V_L$ domain of the protease sensitive scFv comprises SEQ ID NO: 34.

In various embodiments, the CAR comprises: a transmembrane domain selected from: a CD4 transmembrane domain or variant thereof having 1-5 amino acid modifications, a CD8 transmembrane domain or variant thereof having 1-5 amino acid modifications, a CD28 transmembrane domain or a variant thereof having 1-5 amino acid modifications; a costimulatory domain selected from: a 4-IBB costimulatory domain or a variant thereof having 1-5 amino acid modifications and an CD28 costimulatory domain or a variant thereof having 1-5 amino acid modifications; a CD3ζ signaling domain of a variant thereof having 1-5 amino acid modifications; and a spacer region having 20-150 amino acids located between the scFv and the transmembrane domain.

In various embodiments: The nucleic acid molecule of claim 1, wherein the costimulatory domain is selected from the group consisting of: a 4-IBB costimulatory domain and variants thereof having 1-5 amino acid modifications; the transmembrane domain is a CD4 transmembrane domain or variant thereof having 1-5 amino acid modifications; the transmembrane domain is a CD4 transmembrane domain; the CAR comprises two different costimulatory domains selected from the group consisting of: a CD28 costimulatory domain or a variant thereof having 1-5 amino acid modifications, a 4-IBB costimulatory domain or a variant thereof having 1-5 amino acid modifications and an OX40 costimulatory domain or a variant thereof having 1-5 amino acid modifications; the chimeric antigen receptor comprises a CD44v6-binding scFv having the amino acid sequence of SEQ ID NO:1 or a variant thereof having 1-2 amino acid modifications; a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications, and a CD3ζ transmembrane domain or a variant thereof having 1-2 amino acid modifications; a 4-1BB costimulatory domain; or a variant thereof having 1-2 amino acid modifications; and CD3ζ signaling domain or a variant thereof having 1-2 amino acid modifications; and a spacer region having 20-150 amino acids located between the scFv and the transmembrane domain; the spacer region comprises an amino acid sequence selected from the group consisting of SEQ ID NOs: 2-12 or a variant thereof having 1-5 amino acid modifications; the spacer comprises an IgG hinge region; the spacer comprises 10-50 amino acids; the 4-1BB costimulatory domain comprises the amino acid sequence of SEQ ID NO: 24 or a variant thereof having 1-5 amino acid modifications; the CD3ζ signaling domain comprises the amino acid sequence of SEQ ID NO:21; a linker of 3 to 15 amino acids is located between the costimulatory domain and the CD3ζ signaling domain or variant thereof; and the CAR comprises the amino acid sequence of SEQ ID NO: 29 or 30 or a variant thereof having 1-5 amino acid modifications.

Also described here is an expression vector and a viral vector comprising the nucleic acid molecules described herein. Also described is a population of human T cells transduced by a vector comprising a nucleic acid molecule described herein. Also described is a method of treating cancer in a patient comprising administering a population of autologous or allogeneic human T cells transduced by a vector comprising a nucleic acid molecule described herein. In embodiments of the method: the population of human T cells comprise central memory T cells; MMP-2 or MMP-9 is present in the tumor microenvironment; the patient is suffering from a leukemia or lymphoma; and the patient is suffering from AML or multiple myeloma.

The approach used for CD44v6 CAR can be used with any target for treating cancer where the tumor microenvironment has proteases such as MMP-2 or MMP-9.

In various embodiments: the chimeric antigen receptor comprises: a CD44v6 scFv (e.g., an scFv comprising the amino acid sequence EVQLVESGGGLVKPGGSLRLS-CAASGFTFSSYDMSWVRQAPGKGLEWVSTISSG GSYTYYLDSIKGRFTISRDNAKNSLYLQMNSLRAED-TAVYYCARQGLDYWGRG TLVTVSSGGGGSGGGGSGGGGSEIVLTQSPATLSL-SPGERATLSCSASSSINYIYW YQQKPGQAPRLLIYLT-SNLASGVPARFSGSGSGTDFTLTISSLEPEDFAVYY-CLQW SSNPLTFGGGTKVEIK (SEQ ID NO:1) with up to 10 single amino acid substitutions); a spacer region; a CD28 transmembrane domain; a CD28 co-signaling domain; and a CD3ζ signaling domain; the chimeric antigen receptor comprises: a CD44v6 scFv; a spacer region; a CD4 transmembrane domain; a 4-1BB co-signaling domain; and a CD3ζ signaling domain; the chimeric antigen receptor comprises: a CD44v6 scFv; a spacer region comprising an amino acid sequence selected from SEQ ID Nos:2-5 and 9-12; a CD4 transmembrane domain; a 4-1BB co-signaling domain; and a CD3ζ signaling domain; the chimeric antigen receptor comprises: a CD44v6 scFv; a spacer region comprising an amino acid sequence selected from SEQ ID Nos:2-5 and 9-12; a CD28 transmembrane domain; a CD28 co-signaling domain; and a CD3ζ signaling domain; the chimeric antigen receptor comprises: a CD44v6 scFv; a spacer a spacer comprising an amino acid sequence selected from SEQ ID Nos:2-5 and 9-12; CD4 transmembrane domain; a 4-1BB co-signaling domain; and CD3ζ signaling domain; the chimeric antigen receptor comprises: a spacer a spacer comprising an amino acid sequence selected from SEQ ID Nos:2-5 and 9-12; a CD28 transmembrane domain; a CD28 co-signaling domain; and a CD3ζ signaling domain; the chimeric antigen receptor comprises an amino acid sequence at least 95% identical to an amino acid sequence selected from: SEQ ID NOs: 20-40; the chimeric antigen receptor comprises an amino acid sequence identical to an amino acid sequence selected from: SEQ ID NOs: 29-30; the chimeric antigen receptor comprises an amino acid sequence identical to an amino acid sequence selected from: SEQ ID NOs: 29-40, each with no more than 5 single amino acid substitutions; at least 20%, 30%, or 40% of the transduced human T cells are central memory T cells; at least 30% of the transduced human T cells are CD4+ and CD62L+ or CD8+ and CD62L+; the population of human T cells are autologous to the patient; and the population of human T cells are allogenic to the patient.

The protease sensitive scFv can comprise the sequence of SEQ ID NO:1 wherein the linker (GGGGSGGGGSGGGG; SEQ ID NO: 37) is replaced by a protease sensitive linker, for example, a linker sensitive to MMP-2 (e.g., GSTSGSKG PLGLAGATKG; SEQ ID NO: 35) or MMP-9 (e.g., GST-SGSKGPKGLKGATKG; SEQ ID NO: 36).

DESCRIPTION OF DRAWINGS

FIG. 9: Amino acid sequence of a CD44v6 CAR. The amino acid sequence presented is the amino acid sequence of a CD44v6 CAR, including the signal sequence, together with the sequence of the truncated EGFR sequence used for monitoring CAR expression and the T2A ribosomal skip sequence that allows the CAR to be co-expressed, but not fused to the truncated EGFR sequence (SEQ ID NO:35). The immature CAR includes: GMCSFR signal peptide, a CD44v6 scFv, an IgG4 derived sequence that acts as a spacer, a CD4 transmembrane domain, a 4-IBB co-stimulatory domain that includes a LL to GG sequence alteration, a three Gly sequence, a CD3 Zeta stimulatory domain. The transcript also encodes a T2A ribosomal sequence and a truncated EGFR sequence that are not part of the CAR protein sequence. The mature CAR is identical to the immature CAR, but lacks the GMCSF signal peptide. The various domains are indicated.

FIG. 10: Amino acid sequences of CD44v6 scFv. (A) CD44v6 scFv with MMP-2 sensitive linker (SEQ ID NO:38). (B) CD44v6 scFv with MMP-9 sensitive linker (SEQ ID NO: 39). (C) CD44v6 scFv VH domain (SEQ ID NO:33). (D) CD44v6 scFv VL domain (SEQ ID NO:34).

DETAILED DESCRIPTION

CD44v6 Targeted CAR

Figure 1:
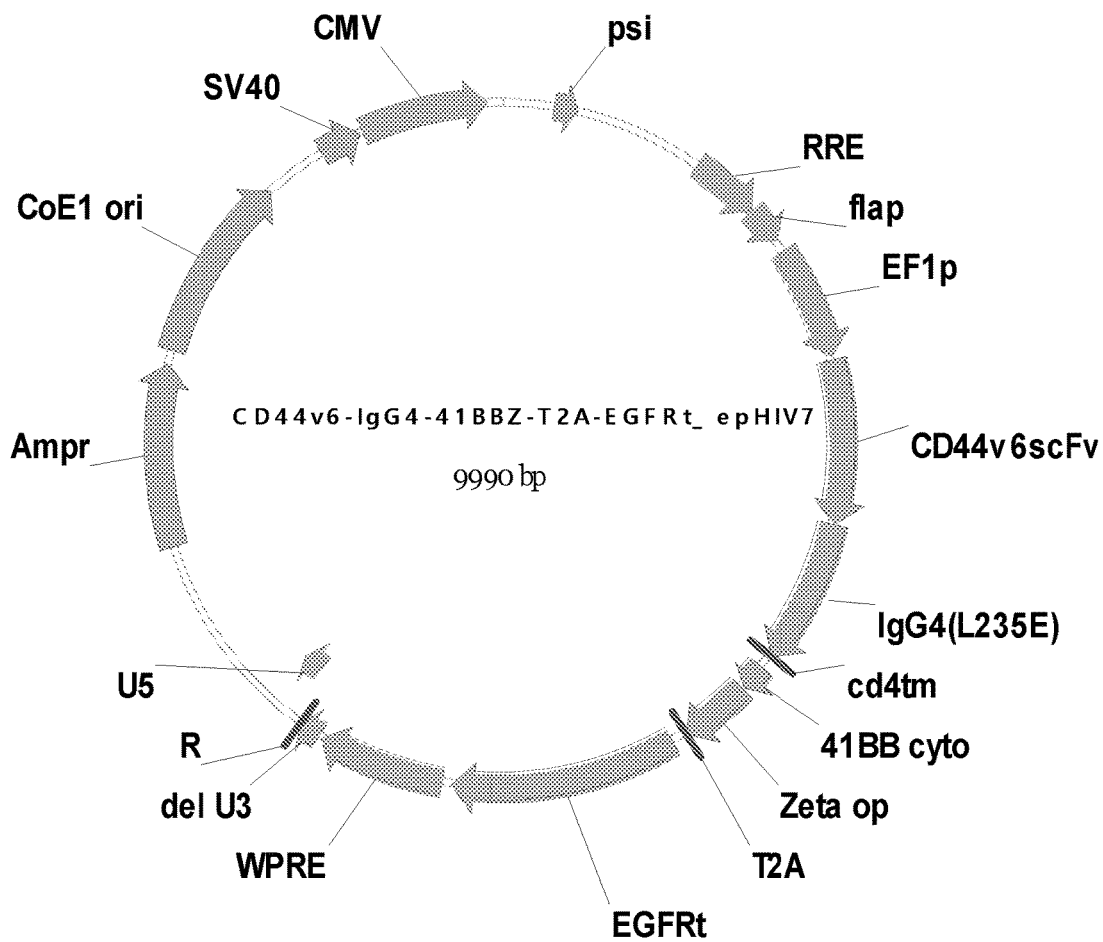
FIG. 1: CD44v6R-41BBZ-T2A-huEGFRt construct contained in SIN lentiviral vector. Diagram of the CD44v6R: 41BB:zeta-T2A-EGFRt construct, where the CD44v6-specific ScFv, IgG4 Fc hinge, CD4 transmembrane, 41BB and CD3z cytoplasmic signaling domains of the CD44v6R: 41BB:zeta CAR, as well as the T2A ribosome skip and truncated huEGFR sequences are indicated. This vector, which expresses the CAR used in the studies described below, does not express a soluble scFv targeted to CD44v6.

The CD44v6-targeted CAR described herein include a CD44v6-targeting scFv (e.g., an (e.g., an scFv comprising the amino acid sequence EVQLVESGGGLVKPGGSLRLS-CAASGFTFSSYDMSWVRQAPGKGLEWVSTISSG GSYTYYLDSIKGRFTISRDNAKNSLYLQMNSLRAED-TAVYYCARQGLDYWGRG TLVTVSSGGGGSGGGGSGGGGSEIVLTQSPATLSL-SPGERATLSCSASSSINYIYW YQQKPGQAPRLLIYLT-SNLASGVPARFSGSGSGTDFTLTISSLEPEDFAVYY-CLQW SSNPLTFGGGTKVEIK (SEQ ID NO:1) or comprising the heavy chain sequence EVQLVESGG-GLVKPGGSLRLSCAASGFTFSSYDMSWVRQAPGK-GLEWVSTISSG GSYTYYLDSIKGRFTISRDNAKNS-LYLQMNSLRAEDTAVYYCARQGLDYWGRG TLVTVSS (SEQ ID NO:33) and the light chain sequence EVQLVESGGGLVKPGGSLRLS-CAASGFTFSSYDMSWVRQAPGKGLEWVSTISSG GSYTYYLDSIKGRFTISRDNAKNSLYLQMNSLRAED-TAVYYCARQGLDYWGRG TLVTVSS (SEQ ID NO:34).

Useful CD44v6 CAR consist of or comprises the amino acid sequence of SEQ ID NO:29 (mature CAR lacking a signal sequence, T2A skip sequence and EGFRt) or the CD44v6 CAR consists of or comprises the amino acid sequence of SEQ ID NO: 30 (immature CAR having a GMCSFRa signal sequence, but lacking T2A skip sequence and EGFRt). The CAR and can be expressed in a form that includes a signal sequence, e.g., a human GM-CSF receptor alpha signal sequence (MLLLVTSLLLCELPHPAFLLIP; SEQ ID NO:26). The CAR can be expressed with additional sequences that are useful for monitoring expression, for example a T2A skip sequence and a truncated EGFRt. Thus, the CAR can comprise or consist of the amino acid sequence of any of SEQ ID Nos: 29-30 or can comprise or consist of an amino acid sequence that is at least 95%, 96%, 97%, 98% or 99% identical to any of SEQ ID Nos: 29-30. The CAR can comprise or consist of the amino acid sequence of any of SEQ ID Nos: 29-30 with up to 1, 2, 3, 4 or 5 amino acid changes (preferably conservative amino acid changes).

Spacer Region

The CAR described herein can include a spacer located between the CD44v6 targeting domain (i.e., a gp120-targeted ScFv or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |

TABLE 1 -continued

Examples of Spacers

| Name | Length | Sequence |
|---|---|---|
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P)+ linker | 22 aa | ESKYGPPCPPCPGGGSSGGGSG (SEQ ID NO: 5) |
| CD28 hinge | 39 aa | IEVMYPPPYLDNEKSNGTIIHVKGKHLCPSPLFPGPSKP (SEQ ID NO: 6) |
| CD8 hinge-48aa | 48 aa | AKPTTTPAPRPPTPAPTIASQPLSLRPEACRPAAGGAVH TRGLDFACD (SEQ ID NO: 7) |
| CD8 hinge-45aa | 45aa | TTTPAPRPPTPAPTIASQPLSLRPEACRPAAGGAVHTRG LDFACD (SEQ ID NO: 8) |
| IgG4(HL-CH3) (includes S228P in hinge) | 129 aa | ESKYGPPCPPCPGGGSSGGGSGGQPREPQVYTLPPSQEE MTKNQVSLTCLVKGFYPSDIAVEWESNGQPENNYKTTPP VLDSDGSFFLYSRLTVDKSRWQEGNVFSCSVMHEALHNH YTQKSLSLSLGK (SEQ ID NO: 9) |
| IgG4(L235E, N297Q) | 229 aa | ESKYGPPCPSCPAPEFEGGPSVFLFPPKPKDTLMISRTP EVTCVVVDVSQEDPEVQFNWYVDGVEVHQAKTKPREEQF QSTYRVVSVLTVLHQDWLNGKEYKCKVSNKGLPSSIEKT ISKAKGQPREPQVYTLPPSQEEMTKNQVSLTCLVKGFYP SDIAVEWESNGQPENNYKTTPPVLDSDGSFFLYSRLTVD KSRWQEGNVFSCSVMHEALHNHYTQKSLSLSLGK (SEQ ID NO: 10) |
| IgG4(S228P, L235E, N297Q) | 229 aa | ESKYGPPCPPCPAPEFEGGPSVFLFPPKPKDTLMISRTP EVTCVVVDVSQEDPEVQFNWYVDGVEVHQAKTKPREEQF QSTYRVVSVLTVLHQDWLNGKEYKCKVSNKGLPSSIEKT ISKAKGQPREPQVYTLPPSQEEMTKNQVSLTCLVKGFYP SDIAVEWESNGQPENNYKTTPPVLDSDGSFFLYSRLTVD KSRWQEGNVFSCSVMHEALHNHYTQKSLSLSLGK (SEQ ID NO: 11) |
| IgG4(CH3) | 107 aa | GQPREPQVYTLPPSQEEMTKNQVSLTCLVKGFYPSDIAV EWESNGQPENNYKTTPPVLDSDGSFFLYSRLTVDKSRWQ EGNVFSCSVMHEALHNHYTQKSLSLSLGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3).

The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO:12). Thus, the entire linker/spacer region can comprise the sequence: ESKYGPPCPPCPGGGSSGGGSGGQPREPQVYTLPPSQEEMTKNQVSLTCLVKGFYPSDIAVEWESNGQPENNYKTTPPVLDSDGSFFLYSRLTVDKSRWQEGNVFSCSVMEIEALHNHYTQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the. Table 2 includes examples of suitable transmembrane domains. Where a spacer region is present, the transmembrane domain is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27aa | FWVLVVVGGVLACYSLLVTVA FIIFWV (SEQ ID NO: 14) |
| CD28(M) | NM_006139 | 28aa | MFWVLVVVGGVLACYSLLVTV AFIIFWV (SEQ ID NO: 15) |

TABLE 2 -continued

Examples of Transmembrane Domains

| Name | Accession | Length | Sequence |
|---|---|---|---|
| CD4 | M35160 | 22aa | MALIVLGGVAGLLLFIGLGIFF (SEQ ID NO: 16) |
| CD8tm | NM_001768 | 21aa | IYIWAPLAGTCGVLLLSLVIT (SEQ ID NO: 17) |
| CD8tm2 | NM_001768 | 23aa | IYIWAPLAGTCGVLLLSLVITLY (SEQ ID NO: 18) |
| CD8tm3 | NM_001768 | 24aa | IYIWAPLAGTCGVLLLSLVITLYC (SEQ ID NO: 19) |
| 41BB | NM_001561 | 27aa | IISFFLALTSTALLFLLFFLTLRF SVV (SEQ ID NO: 20) |

Costimulatory Domain

The costimulatory domain can be any domain that is suitable for use with a CD3ζ signaling domain. In some cases, the costimulatory domain is a CD28 costimulatory domain that includes a sequence that is at least 90%, at least 95%, at least 98% identical to or identical to: RSKRSRGGHSDYMNMTPRRPGPTRKHYQPYAPPRD-FAAYRS (SEQ ID NO:23; LL to GG amino acid change double underlined). In some cases, the CD28 co-signaling domain has 1, 2, 3, 4 of 5 amino acid changes (preferably conservative and preferably not in the underlined GG sequence) compared to SEQ ID NO:23. In some cases the co-signaling domain is a 4-1BB co-signaling domain that includes a sequence that is at least 90%, at least 95%, at least 98% identical to or identical to: KRGRKKLLY-IFKQPFMRPVQTTQEEDGCSCRFPEEEEGGCEL (SEQ ID NO:24). In some cases, the 4-1BB co-signaling domain has 1, 2, 3, 4 or 5 amino acid changes (preferably conservative) compared to SEQ ID NO:24.

The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLYNE LNLGRREEYDVLDKRRGRDPEMG GKPRRKNPQEGLVNELQKDKMAE AYSEIGMKGERRRGKGHDGLYQG LSTATKDTYDALHMQALPPR (SEQ ID NO: 21) |
| CD28 | NM_006139 | 42aa | RSKRSRLLHSDYMNMTPRRPGPT RKHYQPYAPPRDFAAYRS (SEQ ID NO: 22) |
| CD28gg* | NM_006139 | 42aa | RSKRSRGGHSDYMNMTPRRPGPT RKHYQPYAPPRDFAAYRS (SEQ ID NO: 23) |
| 41BB | NM_001561 | 42 aa | KRGRKKLLYIFKQPFMRPVQTTQ EEDGCSCRFPEEEEGGCEL (SEQ ID NO: 24) |

TABLE 3 -continued

CD3ζ Domain and Examples of Costimulatory Domains

| Name | Accession | Length | Sequence |
|---|---|---|---|
| OX40 | | 42 aa | ALYLLRRDQRLPPDAHKPPGGGS FRTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and in some cases a short linker consisting of 2-10, e.g., 3 amino acids (e.g., GGG) is positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to: RVKFSRSADAPAYQQGQNQLYNELNLGR-REEYDVLDKRRGRDPEMGGKPRRK NPQEGLY-NELQKDKMAEAYSEIGMKGERRRGKGHDGLYQGL-STATKDTYDAL HMQALPPR (SEQ ID NO:21). In some cases, the CD3ζ signaling has 1, 2, 3, 4 of 5 amino acid changes (preferably conservative) compared to SEQ ID NO:21.

Truncated EGFR

The CD3ζ signaling domain can be followed by a ribosomal skip sequence (e.g., LEGGGEGRGSLLTCGD-VEENPGPR; SEQ ID NO:27) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDLHIL PVAFRGDSFTHTPPLDPQELDI-
LKTVKEITGFLLIQAWPENRTDLHAFENLEIIRGR TKQHGQFSLAVVSLNITSLGLRSLKEISDGDVIIS-GNKNLCYANTINWKKLFGTSG QKTKIISNRGENSCK-ATGQVCHALCSPEGCWGPEPRDCVSCRNVSR-GRECVDKC
NLLEGEPREFVENSECIQCHPECLPQAMNITCT-GRGPDNCIQCAHYIDGPHCVKT CPAGVM-GENNTLVWKYADAGHVCHLCHPNCTYGCTGPG-LEGCPTNGPKIPSIA TGMVGALLLLLVVALGIGLFM (SEQ ID NO:28). In some cases, the truncated EGFR has 1, 2, 3, 4 of 5 amino acid changes (preferably conservative) compared to SEQ ID NO:28.

CD44v6 Targeted CAR

FIG. 9 depicts the amino acid sequence of a CD44v6 targeted CAR together with a truncated EGFR that can be used as a marker, which is joined to the CAR sequence via a T2A skip sequence. The truncated EGFR is expressed by cells that express the CAR and in this way serves as a marker and as a means to target CAR expressing cells. The sequence also includes a GMSCFRa signal sequence, that like the EGFRt sequence that are not present in the mature CAR as expressed on T cells. described herein. Useful CAR include hose that comprise or consist of the amino acid sequence of any of SEQ ID Nos: 29-30 or an amino acid sequence that is at least 95%, 96%, 97%, 98% or 99% identical to any of SEQ ID Nos: 29-30 or the amino acid sequence of any of SEQ ID Nos: 29-30 with up to 1, 2, 3, 4 or 5 amino acid changes (preferably conservative amino acid changes). In various embodiments: the population of human T cells are CD8+ cells.

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

The CAR can include a sequence that is at least 90%, at least 95%, at least 98% identical to or identical to the mature amino acid sequence depicted in FIG. 9 (SEQ ID Nos: 29-40), either including or excluding the GMCSFRa signal sequence and either including or excluding the T2A ribosomal skip sequence and the truncated EGFRt).

In some cases, the CD44v6 CAR can be produced using a vector in which the CAR open reading frame is followed by a T2A ribosome skip sequence and a truncated EGFR (EGFRt), which lacks the cytoplasmic signaling tail. In this arrangement, co-expression of EGFRt provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt incorporated in the CD44v6CAR lentiviral vector can act as suicide gene to ablate the CAR+T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of an CD44v6 CAR as well as a non-immunogenic surface marker for in vivo detection, ablation, and potential ex vivo selection. The activated/genetically modified CD44v6 central memory T cells can be expanded in vitro with IL-2/IL-15 and then cryopreserved.

Example 1: Preparation and Characterization of CD44v6 CAR

CD44v6R-41BBZ-T2A-huEGFRt construct contained in SIN lentiviral vector. A lentiviral construct was prepared using the approach described in Wang et al. (*Blood* 118: 1255, 2011). FIG. 1 is a diagram of the CD44v6R:41BB:zeta-T2A-EGFRt construct, where the CD44v6-specific ScFv, IgG4 Fc hinge, CD4 transmembrane, 41BB and CD3z cytoplasmic signaling domains of the CD44v6R:41BB:zeta CAR, as well as the T2A ribosome skip and truncated huEGFR sequences are indicated. This vector, which expresses the CAR used in the studies described below, does not express a soluble scFv targeted to CD44v6.

Figure 2:
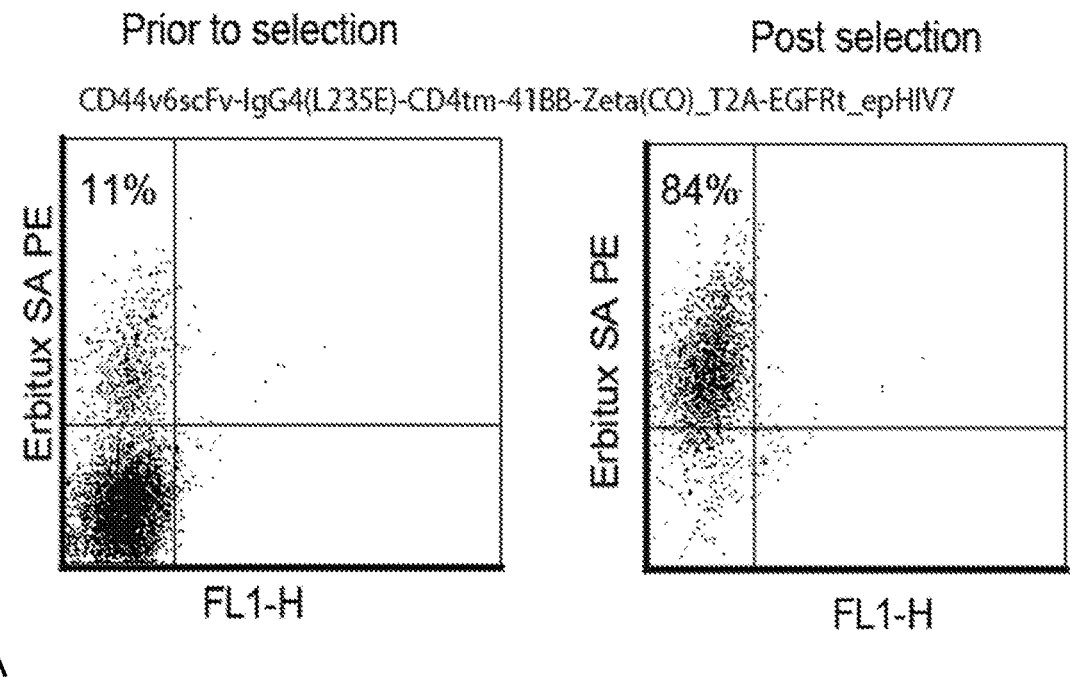
FIG. 2 Purification and expansion of $CD8^+T_{CM}$ derived CD44v6CAR/EGFRt T cells. (A) $CD8^+$ central memory T cells ($CD62L^+CD45RO^+CD8^+$; $CD8^+T_{CM}$) were isolated from a healthy donor and transduced with lentivirus encoding CD44v6CAR/EGFRt after CD3/CD28 beads activation. (A) Gene modified cells were immunomagnetically purified after labeling with biotinylated Erbitux followed by anti-biotin microbeads and expanded in rapid expansion medium (REM) containing OKT3 and feeder cells in the presence of IL-2 (50 U/ml) and IL-15 (1 ng/ml). (B) Fold expansion of purified CD44v6CAR T cells after each cycle of REM stimulation.
Figure 2:
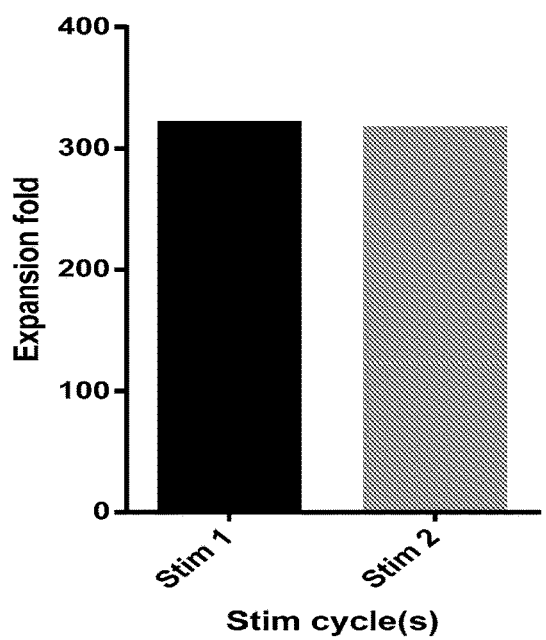

Purification and expansion of $CD8^+T_{CM}$ derived CD44v6CAR/EGFRt T cells. $CD8^+$ central memory T cells ($CD62L^+CD45RO^+CD8^+$; $CD8^+T_{CM}$) were isolated from a healthy donor and transduced with lentivirus encoding CD44v6CAR/EGFRt after CD3/CD28 beads activation using the approach described in Wang et al. (*Blood* 117: 1888, 2011). Gene modified cells were immunomagnetically purified after labeling with biotinylated Erbitux followed by anti-biotin microbeads and expanded in rapid expansion medium (REM) containing OKT3 and feeder cells in the presence of IL-2 (50 U/ml) and IL-15 (1 ng/ml) (FIG. 2A). FIG. 2B shows the fold expansion of purified CD44v6CAR T cells after each cycle of REM stimulation.

Figure 3:
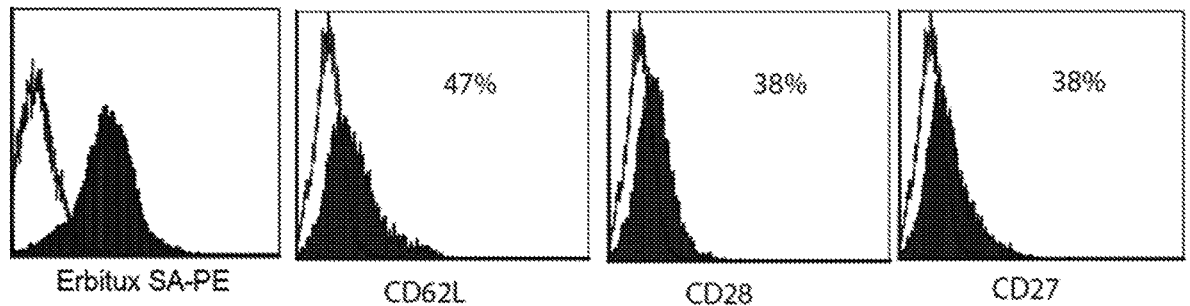
FIG. 3 Phenotype of ex vivo expanded CD44v6CAR/ EGFRt $CD8^+$ T cells Gene modified cells were immunomagnetically purified after labeling with biotinylated Erbitux followed by anti-biotin microbeads and expanded in rapid expansion medium (REM) containing OKT3 and feeder cells in the presence of IL-2 (50 U/ml) and IL-15 (1 ng/ml). After 2 cycles of in vitro expansion, T cells were labeled with antibodies against EGFRt (Erbitux), CD62L, CD28 and CD27. % Positive cells (closed histogram) over isotype controls (open histogram) are presented.

Phenotype of ex vivo expanded CD44v6CAR/EGFRt $CD8^+$ T cells. Gene modified cells were immunomagnetically purified after labeling with biotinylated Erbitux followed by anti-biotin microbeads and expanded in rapid expansion medium (REM) containing OKT3 and feeder cells in the presence of IL-2 (50 U/ml) and IL-15 (1 ng/ml). After 2 cycles of in vitro expansion, T cells were labeled with antibodies against EGFRt (Erbitux), CD62L, CD28 and CD27. The results of this analysis are presented in FIG. 3 where the % Positive cells (closed histogram) over isotype controls (open histogram) are reported.

Figure 4:
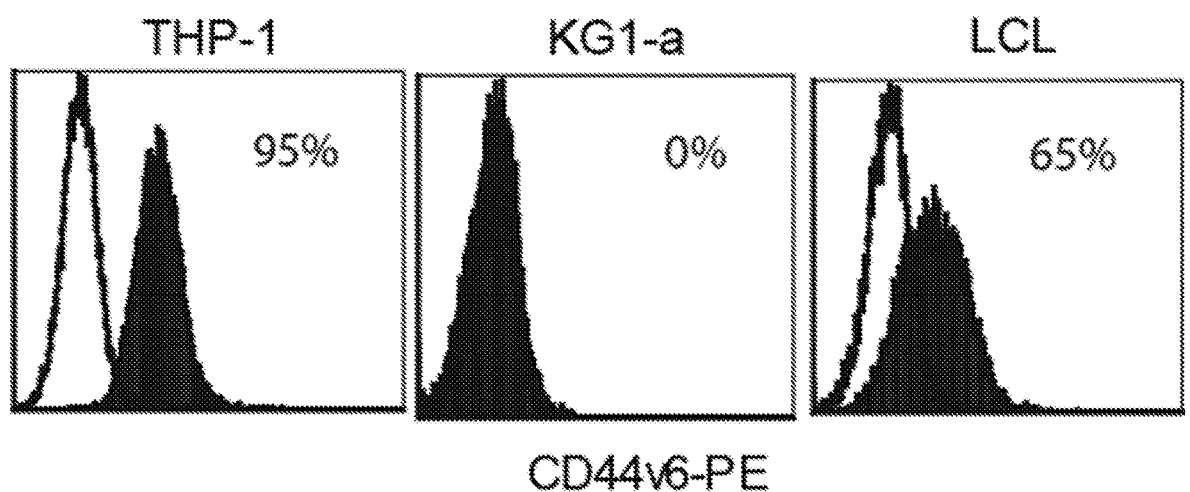
FIG. 4: CD44v6 expression on leukemic cells. AML (THP-1 and KG1a) and B cell lymphoma (LCL) cells were labeled with PE-conjugated CD44v6 Ab (clone 2F10) (closed histogram) and isotype control Ab (open histogram) and analyzed by flow cytometry. % Positive cells over isotype controls are presented.

CD44v6 expression on leukemic cells. AML (THP-1 and KG1a) and B cell lymphoma (LCL) cells were labeled with PE-conjugated CD44v6 Ab (clone 2F10) and isotype control Ab and analyzed by flow cytometry. The results of this analysis are presented in FIG. 4 where the % Positive cells over isotype controls are presented.

Figure 5:
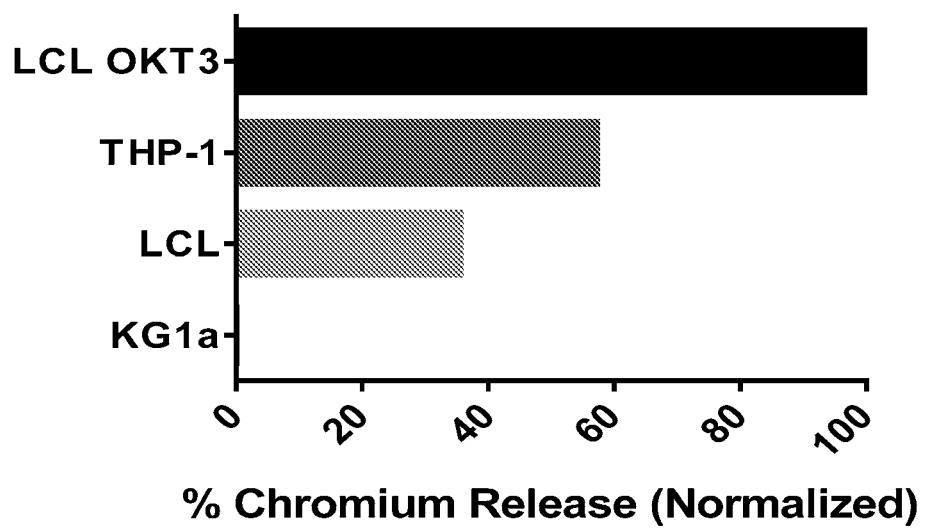
FIG. 5: Cytolytic activity of CD44v6CAR/EGFRt $CD8^+$ T cells After 2 cycles of in vitro expansion, CD44v6CAR/ EGFRt $CD8^+$ T cells were incubated for 4 hrs with 51Cr-labeled THP-1 or LCL cells, or OKT3-expressing LCL (LCLOKT3) cells as positive targets and CD44v6 negative KG1a cells as negative targets at 25:1 E:T ratios. Mean percent cytotoxicity of triplicate wells that was normalized over LCL OKT3 is depicted.

Cytolytic activity of CD44v6CAR/EGFRt CD8+ T cells. After 2 cycles of in vitro expansion, CD44v6CAR/EGFRt CD8+ cells were incubated for 4 hrs with 51Cr-labeled THP-1 or LCL cells, or OKT3-expressing LCL (LCLOKT3) cells as positive targets and CD44v6 negative KG1a cells as negative targets at 25:1 E:T ratios. The results of this analysis are presented in FIG. 5.

Figure 6:
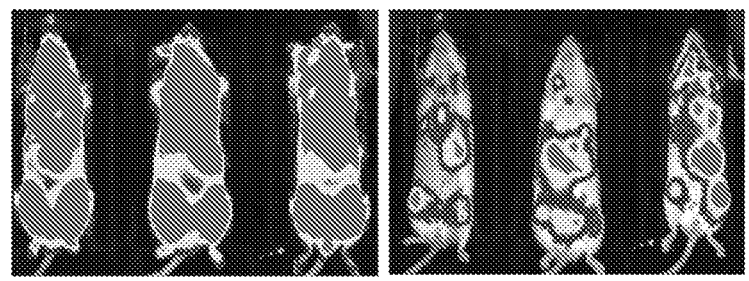
FIG. 6: Anti-lymphoma effects of adoptively transferred CD8$^+$T$_{CM}$ derived CD44v6CAR/EGFRt T cells. 2×10$^6$ CD19$^+$ffluc$^+$ lymphoblastoid cell lines (LCL) cells were injected (i.v) into NSG mice on day-3. Subsequently, 5×10$^6$ CD8$^+$T$_{CM}$ derived CD44v6CAR T cells were intravenously infused into the tumor bearing mice on day 0. Recipient mice received intraperitoneal injection of irradiated human IL15 secreting NSO cells to support human T cell persistence. Tumor signals were monitored by biophotonic imaging. (A) Representative images on day 14 are presented. (B) Mean±SEM of phonton/sec from multiple mice are depicted.
Figure 6:
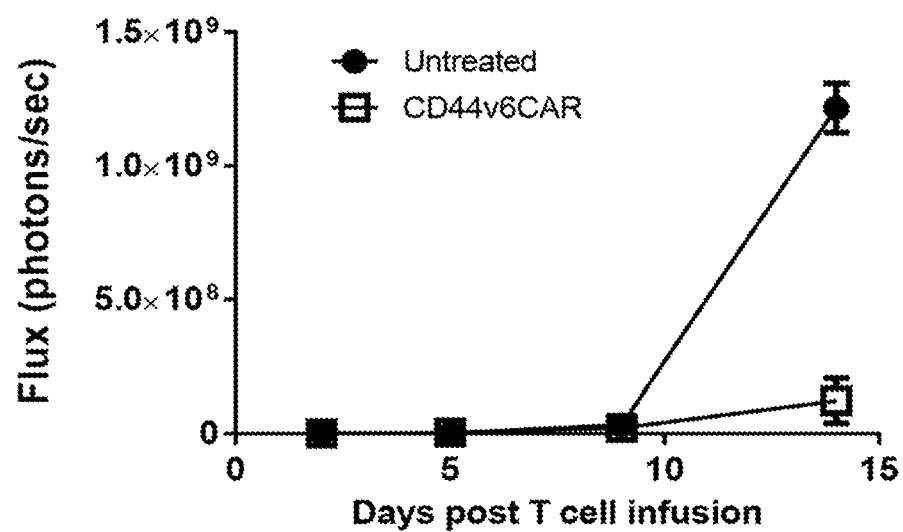

Anti-lymphoma effects of adoptively transferred CD8+ $T_{CM}$ derived CD44v6CAR/EGFRt T cells. The examine the anti-lymphoma effect of adoptively transferred CD8+TCM derived CD44v6CAR/EGFRt T cells, $2\times10^6$ CD19+ffluc+ lymphoblastoid cell lines (LCL) cells were injected (i.v) into NSG mice on day-3. Subsequently, $5\times10^6$ CD8+$T_{CM}$ derived CD44v6CAR T cells were intravenously infused into the tumor bearing mice on day 0. Recipient mice received intraperitoneal injection of irradiated human IL15 secreting NSO cells to support human T cell persistence. Tumor signals were monitored by biophotonic imaging. The results of this analysis are presented in FIG. 6.

Figure 7:
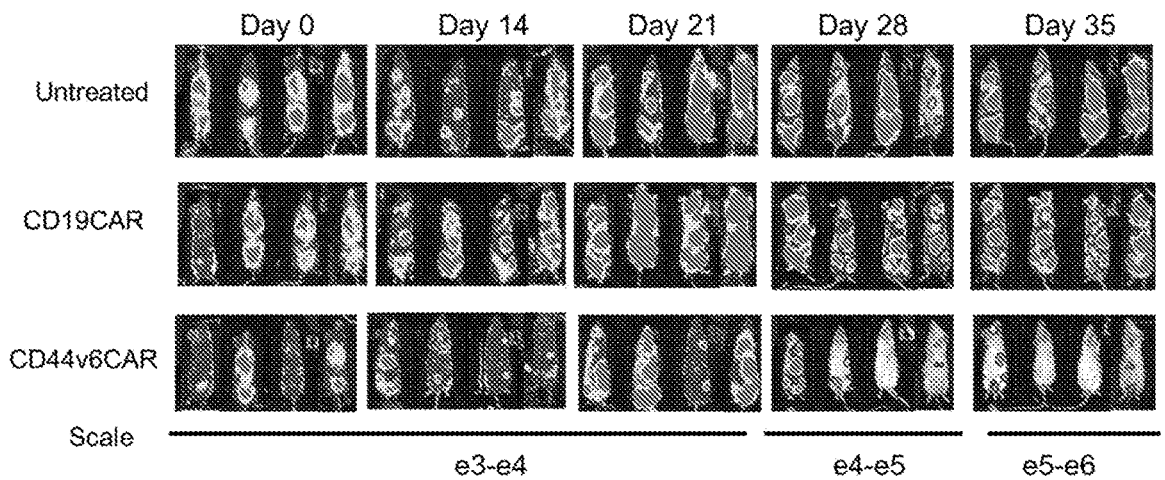
FIG. 7: Anti-AML effects of adoptively transferred CD8$^+$ T$_{CM}$ derived CD44v6CAR/EGFRt T cells 1.5×10$^6$ GFPffluc$^+$AML cells (THP-1) were injected (i.v) into NSG mice on day −3. 5×10$^6$ CD8$^+$T$_{CM}$ derived CD44v6CAR T cells were intravenously infused into the tumor bearing mice on day 0. Mice received no T cells or CD8$^+$T$_{CM}$ derived irrelevant CAR (CD19CAR) T cells from the same donor were used as negative controls. All recipient mice received intraperitoneal injection of irradiated human IL15 secreting NSO cells to support human T cell persistence. (A) Tumor signals were monitored by biophotonic imaging. (B) Means±SEM of phonton/sec from multiple mice are depicted.
Figure 7:
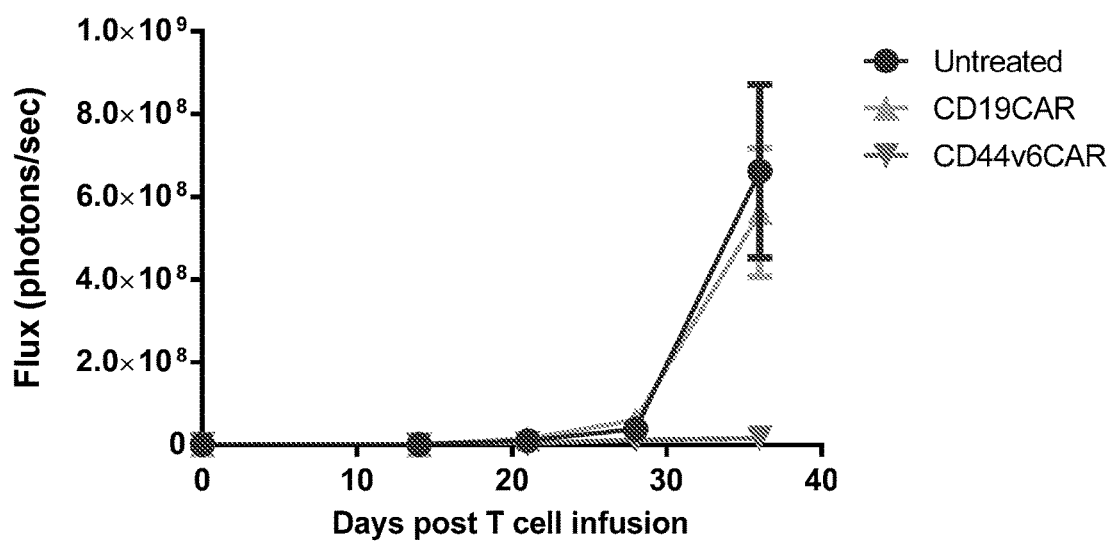

Anti-AML effects of adoptively transferred CD8+$T_{CM}$ derived CD44v6CAR/EGFRt T cells. For this study, $1.5\times10^6$ GFPffluc+ AML cells (THP-1) were injected (i.v) into NSG mice on day-$3.5\times10^6$ CD8+$T_{CM}$ derived CD44v6CAR T cells were intravenously infused into the tumor bearing mice on day 0. Mice received no T cells or CD8+$T_{CM}$ derived irrelevant CAR (CD19CAR) T cells from the same donor were used as negative controls. All recipient mice received intraperitoneal injection of irradiated human IL15 secreting NSO cells to support human T cell persistence. The results are presented in FIG. 7.

Figure 8:
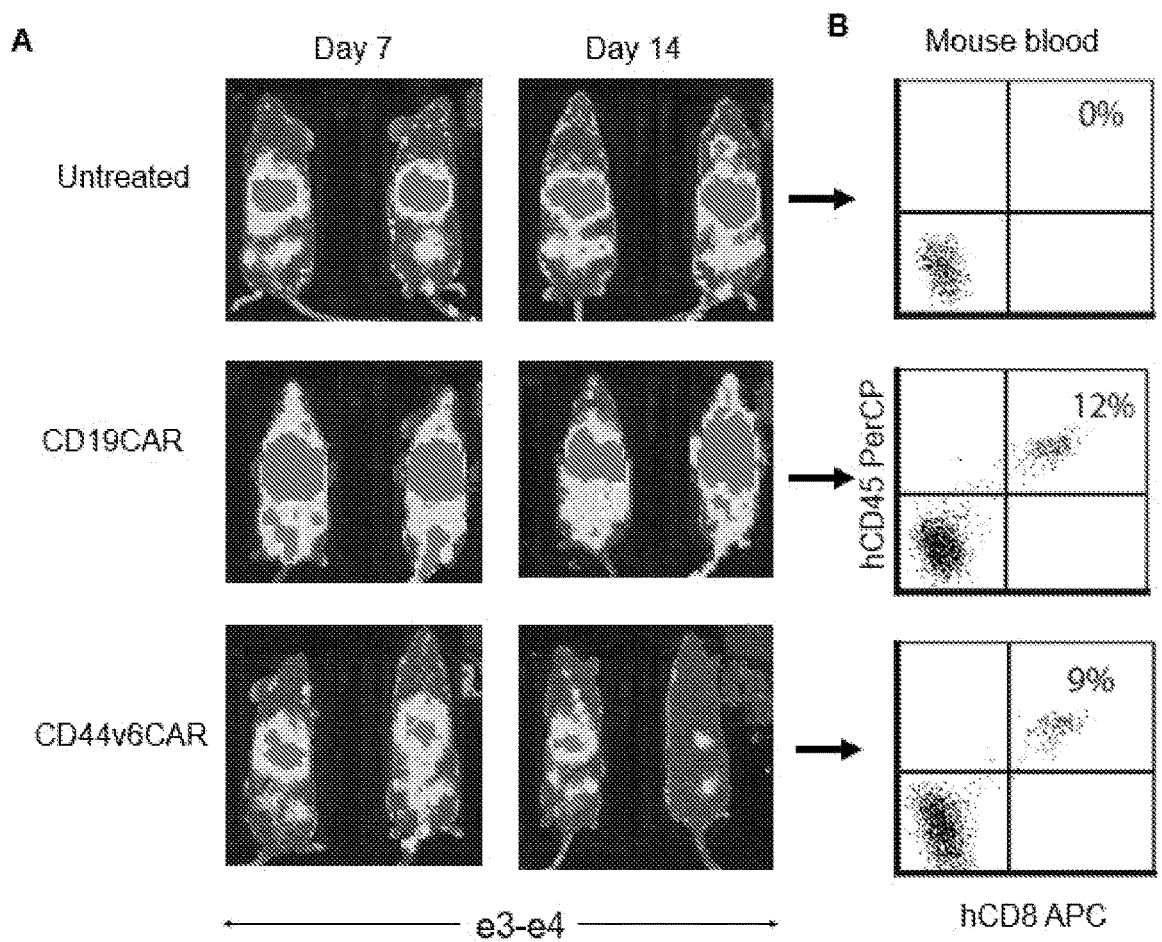
FIG. 8: CD8$^+$T$_{CM}$ derived CD44v6 CAR/EGFRt. T cells interfere with human leukemia initiation in immunodeficient mice 20×10$^6$ CD44v6CAR T cells or irrelevant CAR T cells (CD19CAR) derived from CD8$^+$T$_{CM}$ of the same donor were adoptively transferred (i.v) into NSG mice. 2 weeks post T cell infusion, 1.5×10$^6$ GFPffluc$^+$ THP-1 cells expressing CD44v6 were inoculated (i.v) into the mice. (A) Tumor signals were monitored by biophotonic imaging 7 and 14 days post tumor infusion. (B) % Human T cells in peripheral blood are depicted

CD8+$T_{CM}$ derived CD44v6 CAR/EGFRt T cells interfere with human leukemia initiation in immunodeficient mice. In this study, $20\times10^6$ CD44v6CAR T cells or irrelevant CAR T cells (CD19CAR) derived from CD8+$T_{CM}$ of the same donor were adoptively transferred (i.v) into NSG mice. 2 weeks post T cell infusion, $1.5\times10^6$ GFPffluc+ THP-1 cells expressing CD44v6 were inoculated (i.v) into the mice. The results of this analysis are presented in FIG. 8.

Summary. The results of these studies suggest that targeting CD44v6 with CD44v6 CAR CD8+$T_{CM}$ cells can lead to potent anti-tumor activity upon adoptive transfer in a murine model and that CD44v6 CAR T cells are capable of interfering leukemia initiation by inhibiting leukemic stem cell homing and proliferation.

Example 2: Generation of Protease Sensitive scFv

A selected scFv (e.g., the scFv used in the selected CAR) can be converted to a protease sensitive scFv by replacing the linker between the variable heavy chain and variable light chain portions with a linker that is sensitive to the selected protease, for example, MMP-2 or MMP-9, both of which are overexpressed and accumulated in various tumors. Yeast surface display, a genotype-phenotype linkage strategy for facile screening of protein libraries can be used to select scFv linkers that are appropriately susceptible to cleavage by MMP-2 and/or MMP-9 and allow for proper heavy and light chain association (Gai et al. 2007 *Curr Opin Struct Biol* 17:467-473). Because MMP-2 and MMP-9 are known to be promiscuous (Prudova et al. 2010 *Mol Cell Proteomics* 9:894-911), a library of candidate cleavage sites (residues G-P-X-X-X-X-X-A, $3.3\times10^7$ variants) can be screened as the central portion of the scFv linker. Sequential fluorescence-activated cell sorting (FACS) experiments are employed to: (1) select linker candidates that yield scFvs with equivalent binding activity to the parent scFv, (2) select linker candidates that are cleaved by physiological concentrations of recombinant active MMP-2 and/or MMP-9, and (3) select linker candidates with equivalent serum stability to the parental linker. Successful linker candidates are screened for immunogenicity using the EpiSweep software package (Choi et al. 2017 *Methods in Molecular Biology* 1529: 375, 2017), with mutations made as needed to eliminate T cell epitopes. Once appropriate lead linker candidates are selected, the scFv can undergo affinity maturation using error-prone PCR (Zaccolo et al. 1996 *Mol Biol* 255:589-60324) followed by FACS to select for scFvs with improved binding affinity, an approach that has been employed successfully for scFvs in the past (Tillotson et al. 2013 *Protein Eng Des Sel* 26:101-112). Lead scFvs are cloned into a bicistronic construct encoding for the EF1α promoter, the soluble protease-susceptible scFv, a T2A ribosome skip sequence, and the parental CAR. Off-tumor toxicities of the CAR are evaluated in vitro and in appropriate murine models.

What is claimed is:

1. A nucleic acid molecule comprising: (a) a nucleotide sequence encoding a chimeric antigen receptor (CAR) comprising amino acids 23 to 665 of SEQ ID NO: 31 and (b) a nucleotide sequence encoding a protease sensitive scFv comprising, from amino to carboxy terminus, a VH domain comprising SEQ ID NO: 33 and a VL domain SEQ ID NO:34 joined by a protease-sensitive linker that is sensitive to MMP-2 or MMP-9.

2. An expression vector comprising the nucleic acid molecule of claim 1.

3. A viral vector comprising the nucleic acid molecule of claim 1.

4. A population of human T cells transduced by a vector comprising the nucleic acid molecule of claim 1.

5. A method of treating cancer in a patient comprising administering a population of autologous or allogeneic human T cells transduced by a vector comprising the nucleic acid molecule of claim 1.

6. The method of claim 5, wherein MMP-2 or MMP-9 is present in the tumor microenvironment.

7. The nucleic acid molecule of claim 1, wherein the protease sensitive scFv comprises the amino acid sequence of SEQ ID NO: 38 or SEQ ID NO: 39.

* * * * *

SEQUENCE LISTING

```
<160> NUMBER OF SEQ ID NOS: 39

<210> SEQ ID NO 1
<211> LENGTH: 235
<212> TYPE: PRT
<213> ORGANISM: Artificial Sequence
<220> FEATURE:
<223> OTHER INFORMATION: scFv

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Leu Asp Ser Ile
    50                  55                  60

Lys Gly Arg Phe Thr Ile Ser Arg Asp Asn Ala Lys Asn Ser Leu Tyr
```

-continued

```
                65                  70                  75                  80
Leu Gln Met Asn Ser Leu Arg Ala Glu Asp Thr Ala Val Tyr Tyr Cys
                    85                  90                  95
Ala Arg Gln Gly Leu Asp Tyr Trp Gly Arg Gly Thr Leu Val Thr Val
                100                 105                 110
Ser Ser Gly Gly Gly Gly Ser Gly Gly Gly Ser Gly Gly Gly Gly
                115                 120                 125
Ser Glu Ile Val Leu Thr Gln Ser Pro Ala Thr Leu Ser Leu Ser Pro
            130                 135                 140
Gly Glu Arg Ala Thr Leu Ser Cys Ser Ala Ser Ser Ile Asn Tyr
145                 150                 155                 160
Ile Tyr Trp Tyr Gln Gln Lys Pro Gly Gln Ala Pro Arg Leu Leu Ile
                165                 170                 175
Tyr Leu Thr Ser Asn Leu Ala Ser Gly Val Pro Ala Arg Phe Ser Gly
                180                 185                 190
Ser Gly Ser Gly Thr Asp Phe Thr Leu Thr Ile Ser Ser Leu Glu Pro
                195                 200                 205
Glu Asp Phe Ala Val Tyr Tyr Cys Leu Gln Trp Ser Ser Asn Pro Leu
            210                 215                 220
Thr Phe Gly Gly Gly Thr Lys Val Glu Ile Lys
225                 230                 235

<210> SEQ ID NO 2
<211> LENGTH: 10
<212> TYPE: PRT
<213> ORGANISM: Homo sapiens

<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: spacer

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Homo sapiens

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Artificial Sequence
<220> FEATURE:
<223> OTHER INFORMATION: spacer

<400> SEQUENCE: 5

Glu Ser Lys Tyr Gly Pro Pro Cys Pro Pro Cys Pro Gly Gly Gly Ser
1               5                   10                  15
```

Ser Gly Gly Gly Ser Gly
                20

<210> SEQ ID NO 6
<211> LENGTH: 39
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Homo sapiens

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 8
<211> LENGTH: 45
<212> TYPE: PRT
<213> ORGANISM: Homo sapiens

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 129
<212> TYPE: PRT
<213> ORGANISM: Artificial Sequence
<220> FEATURE:
<223> OTHER INFORMATION: spacer

<400> SEQUENCE: 9

Glu Ser Lys Tyr Gly Pro Pro Cys Pro Pro Cys Pro Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 10
<211> LENGTH: 229
<212> TYPE: PRT
<213> ORGANISM: Artificial Sequence
<220> FEATURE:
<223> OTHER INFORMATION: spacer

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 11
<211> LENGTH: 229
<212> TYPE: PRT
<213> ORGANISM: Artificial Sequence
<220> FEATURE:
<223> OTHER INFORMATION: spacer

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Homo sapiens

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Homo sapiens

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Homo sapiens

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Homo sapiens

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Homo sapiens

<400> SEQUENCE: 17

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 18
<211> LENGTH: 23
<212> TYPE: PRT
<213> ORGANISM: Homo sapiens

<400> SEQUENCE: 18

Ile Tyr Ile Trp Ala Pro Leu Ala Gly Thr Cys Gly Val Leu Leu Leu
1               5                   10                  15

Ser Leu Val Ile Thr Leu Tyr
            20

<210> SEQ ID NO 19

```
<211> LENGTH: 24
<212> TYPE: PRT
<213> ORGANISM: Homo sapiens

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 20
<211> LENGTH: 27
<212> TYPE: PRT
<213> ORGANISM: Homo sapiens

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
                20                  25

<210> SEQ ID NO 21
<211> LENGTH: 112
<212> TYPE: PRT
<213> ORGANISM: Homo sapiens

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 22
<211> LENGTH: 41
<212> TYPE: PRT
<213> ORGANISM: Homo sapiens

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 23
<211> LENGTH: 41
<212> TYPE: PRT
<213> ORGANISM: Homo sapiens

<400> SEQUENCE: 23
```

-continued

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 24
<211> LENGTH: 42
<212> TYPE: PRT
<213> ORGANISM: Homo sapiens

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 25
<211> LENGTH: 42
<212> TYPE: PRT
<213> ORGANISM: Homo sapiens

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile
            35                  40

<210> SEQ ID NO 26
<211> LENGTH: 22
<212> TYPE: PRT
<213> ORGANISM: Homo sapiens

<400> SEQUENCE: 26

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 27
<211> LENGTH: 24
<212> TYPE: PRT
<213> ORGANISM: Homo sapiens

<400> SEQUENCE: 27

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 28
<211> LENGTH: 354
<212> TYPE: PRT
<213> ORGANISM: Homo sapiens

<400> SEQUENCE: 28

```
Leu Val Thr Ser Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
            20                  25                  30

Asp Ser Leu Ser Ile Asn Ala Thr Asn Ile Lys His Phe Lys Asn Cys
            35                  40                  45

Thr Ser Ile Ser Gly Asp Leu His Ile Leu Pro Val Ala Phe Arg Gly
        50                  55                  60

Asp Ser Phe Thr His Thr Pro Pro Leu Asp Pro Gln Glu Leu Asp Ile
65                  70                  75                  80

Leu Lys Thr Val Lys Glu Ile Thr Gly Phe Leu Leu Ile Gln Ala Trp
                85                  90                  95

Pro Glu Asn Arg Thr Asp Leu His Ala Phe Glu Asn Leu Glu Ile Ile
                100                 105                 110

Arg Gly Arg Thr Lys Gln His Gly Gln Phe Ser Leu Ala Val Val Ser
            115                 120                 125

Leu Asn Ile Thr Ser Leu Gly Leu Arg Ser Leu Lys Glu Ile Ser Asp
        130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
                180                 185                 190

His Ala Leu Cys Ser Pro Glu Gly Cys Trp Gly Pro Glu Pro Arg Asp
            195                 200                 205

Cys Val Ser Cys Arg Asn Val Ser Arg Gly Arg Glu Cys Val Asp Lys
        210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
                260                 265                 270

Asp Gly Pro His Cys Val Lys Thr Cys Pro Ala Gly Val Met Gly Glu
            275                 280                 285

Asn Asn Thr Leu Val Trp Lys Tyr Ala Asp Ala Gly His Val Cys His
        290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
                325                 330                 335

Val Gly Ala Leu Leu Leu Leu Leu Val Val Ala Leu Gly Ile Gly Leu
            340                 345                 350

Phe Met
```

<210> SEQ ID NO 29
<211> LENGTH: 643
<212> TYPE: PRT
<213> ORGANISM: Artificial Sequence
<220> FEATURE:
<223> OTHER INFORMATION: Chimeric antigen receptor

<400> SEQUENCE: 29

-continued

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Thr Ile Ser Ser Gly Gly Ser Tyr Thr Tyr Tyr Leu Asp Ser Ile
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Leu Asp Tyr Trp Gly Arg Gly Thr Leu Val Thr Val
            100                 105                 110

Ser Ser Gly Gly Gly Gly Ser Gly Gly Gly Gly Ser Gly Gly Gly Gly
        115                 120                 125

Ser Glu Ile Val Leu Thr Gln Ser Pro Ala Thr Leu Ser Leu Ser Pro
        130                 135                 140

Gly Glu Arg Ala Thr Leu Ser Cys Ser Ala Ser Ser Ile Asn Tyr
145                 150                 155                 160

Ile Tyr Trp Tyr Gln Gln Lys Pro Gly Gln Ala Pro Arg Leu Leu Ile
                165                 170                 175

Tyr Leu Thr Ser Asn Leu Ala Ser Gly Val Pro Ala Arg Phe Ser Gly
            180                 185                 190

Ser Gly Ser Gly Thr Asp Phe Thr Leu Thr Ile Ser Ser Leu Glu Pro
        195                 200                 205

Glu Asp Phe Ala Val Tyr Tyr Cys Leu Gln Trp Ser Ser Asn Pro Leu
    210                 215                 220

Thr Phe Gly Gly Gly Thr Lys Val Glu Ile Lys Glu Ser Lys Tyr Gly
225                 230                 235                 240

Pro Pro Cys Pro Pro Cys Pro Ala Pro Glu Phe Glu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser Gln Glu Asp Pro
275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Arg Leu Thr Val Asp Lys Ser

```
                    420                 425                 430
Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
        450                 455                 460

Met Ala Leu Ile Val Leu Gly Gly Val Ala Gly Leu Leu Leu Phe Ile
465                 470                 475                 480

Gly Leu Gly Ile Phe Phe Lys Arg Gly Arg Lys Lys Leu Leu Tyr Ile
            485                 490                 495

Phe Lys Gln Pro Phe Met Arg Pro Val Gln Thr Thr Gln Glu Glu Asp
        500                 505                 510

Gly Cys Ser Cys Arg Phe Pro Glu Glu Glu Glu Gly Gly Cys Glu Leu
            515                 520                 525

Gly Gly Gly Arg Val Lys Phe Ser Arg Ser Ala Asp Ala Pro Ala Tyr
        530                 535                 540

Gln Gln Gly Gln Asn Gln Leu Tyr Asn Glu Leu Asn Leu Gly Arg Arg
545                 550                 555                 560

Glu Glu Tyr Asp Val Leu Asp Lys Arg Arg Gly Arg Asp Pro Glu Met
            565                 570                 575

Gly Gly Lys Pro Arg Arg Lys Asn Pro Gln Glu Gly Leu Tyr Asn Glu
        580                 585                 590

Leu Gln Lys Asp Lys Met Ala Glu Ala Tyr Ser Glu Ile Gly Met Lys
            595                 600                 605

Gly Glu Arg Arg Arg Gly Lys Gly His Asp Gly Leu Tyr Gln Gly Leu
        610                 615                 620

Ser Thr Ala Thr Lys Asp Thr Tyr Asp Ala Leu His Met Gln Ala Leu
625                 630                 635                 640

Pro Pro Arg

<210> SEQ ID NO 30
<211> LENGTH: 665
<212> TYPE: PRT
<213> ORGANISM: Artificial Sequence
<220> FEATURE:
<223> OTHER INFORMATION: Chimeric antigen receptor

<400> SEQUENCE: 30

Met Leu Leu Leu Val Thr Ser Leu Leu Cys Glu Leu Pro His Pro
1               5                  10                  15

Ala Phe Leu Leu Ile Pro Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Asp Met Ser Trp Val Arg Gln Ala Pro Gly
    50                  55                  60

Lys Gly Leu Glu Trp Val Ser Thr Ile Ser Ser Gly Gly Ser Tyr Thr
65                  70                  75                  80

Tyr Tyr Leu Asp Ser Ile Lys Gly Arg Phe Thr Ile Ser Arg Asp Asn
            85                  90                  95

Ala Lys Asn Ser Leu Tyr Leu Gln Met Asn Ser Leu Arg Ala Glu Asp
        100                 105                 110

Thr Ala Val Tyr Tyr Cys Ala Arg Gln Gly Leu Asp Tyr Trp Gly Arg
    115                 120                 125

Gly Thr Leu Val Thr Val Ser Ser Gly Gly Gly Gly Ser Gly Gly Gly
        130                 135                 140
```

```
Gly Ser Gly Gly Gly Ser Glu Ile Val Leu Thr Gln Ser Pro Ala
145                 150                 155                 160

Thr Leu Ser Leu Ser Pro Gly Glu Arg Ala Thr Leu Ser Cys Ser Ala
            165                 170                 175

Ser Ser Ser Ile Asn Tyr Ile Tyr Trp Tyr Gln Gln Lys Pro Gly Gln
            180                 185                 190

Ala Pro Arg Leu Leu Ile Tyr Leu Thr Ser Asn Leu Ala Ser Gly Val
            195                 200                 205

Pro Ala Arg Phe Ser Gly Ser Gly Ser Gly Thr Asp Phe Thr Leu Thr
            210                 215                 220

Ile Ser Ser Leu Glu Pro Glu Asp Phe Ala Val Tyr Tyr Cys Leu Gln
225                 230                 235                 240

Trp Ser Ser Asn Pro Leu Thr Phe Gly Gly Gly Thr Lys Val Glu Ile
            245                 250                 255

Lys Glu Ser Lys Tyr Gly Pro Pro Cys Pro Pro Cys Pro Ala Pro Glu
            260                 265                 270

Phe Glu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
            290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
            325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
            355                 360                 365

Ser Ser Ile Glu Lys Thr Ile Ser Lys Ala Lys Gly Gln Pro Arg Glu
            370                 375                 380

Pro Gln Val Tyr Thr Leu Pro Pro Ser Gln Glu Glu Met Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Arg
            435                 440                 445

Leu Thr Val Asp Lys Ser Arg Trp Gln Glu Gly Asn Val Phe Ser Cys
            450                 455                 460

Ser Val Met His Glu Ala Leu His Asn His Tyr Thr Gln Lys Ser Leu
465                 470                 475                 480

Ser Leu Ser Leu Gly Lys Met Ala Leu Ile Val Leu Gly Gly Val Ala
            485                 490                 495

Gly Leu Leu Leu Phe Ile Gly Leu Gly Ile Phe Phe Lys Arg Gly Arg
            500                 505                 510

Lys Lys Leu Leu Tyr Ile Phe Lys Gln Pro Phe Met Arg Pro Val Gln
            515                 520                 525

Thr Thr Gln Glu Glu Asp Gly Cys Ser Cys Arg Phe Pro Glu Glu Glu
            530                 535                 540

Glu Gly Gly Cys Glu Leu Gly Gly Gly Arg Val Lys Phe Ser Arg Ser
545                 550                 555                 560
```

Ala Asp Ala Pro Ala Tyr Gln Gln Gly Gln Asn Gln Leu Tyr Asn Glu
                565                 570                 575

Leu Asn Leu Gly Arg Arg Glu Glu Tyr Asp Val Leu Asp Lys Arg Arg
            580                 585                 590

Gly Arg Asp Pro Glu Met Gly Gly Lys Pro Arg Arg Lys Asn Pro Gln
        595                 600                 605

Glu Gly Leu Tyr Asn Glu Leu Gln Lys Asp Lys Met Ala Glu Ala Tyr
    610                 615                 620

Ser Glu Ile Gly Met Lys Gly Glu Arg Arg Arg Gly Lys Gly His Asp
625                 630                 635                 640

Gly Leu Tyr Gln Gly Leu Ser Thr Ala Thr Lys Asp Thr Tyr Asp Ala
                645                 650                 655

Leu His Met Gln Ala Leu Pro Pro Arg
            660                 665

<210> SEQ ID NO 31
<211> LENGTH: 1046
<212> TYPE: PRT
<213> ORGANISM: Artificial Sequence
<220> FEATURE:
<223> OTHER INFORMATION: Chimeric antigen receptor

<400> SEQUENCE: 31

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Ser Tyr Asp Met Ser Trp Val Arg Gln Ala Pro Gly
    50                  55                  60

Lys Gly Leu Glu Trp Val Ser Thr Ile Ser Ser Gly Gly Ser Tyr Thr
65                  70                  75                  80

Tyr Tyr Leu Asp Ser Ile Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Gln Gly Leu Asp Tyr Trp Gly Arg
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Ala
145                 150                 155                 160

Thr Leu Ser Leu Ser Pro Gly Glu Arg Ala Thr Leu Ser Cys Ser Ala
                165                 170                 175

Ser Ser Ser Ile Asn Tyr Ile Tyr Trp Tyr Gln Gln Lys Pro Gly Gln
            180                 185                 190

Ala Pro Arg Leu Leu Ile Tyr Leu Thr Ser Asn Leu Ala Ser Gly Val
        195                 200                 205

Pro Ala Arg Phe Ser Gly Ser Gly Ser Gly Thr Asp Phe Thr Leu Thr
    210                 215                 220

Ile Ser Ser Leu Glu Pro Glu Asp Phe Ala Val Tyr Tyr Cys Leu Gln
225                 230                 235                 240

Trp Ser Ser Asn Pro Leu Thr Phe Gly Gly Gly Thr Lys Val Glu Ile
                245                 250                 255

```
Lys Glu Ser Lys Tyr Gly Pro Pro Cys Pro Pro Cys Pro Ala Pro Glu
            260                 265                 270

Phe Glu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
            290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
            355                 360                 365

Ser Ser Ile Glu Lys Thr Ile Ser Lys Ala Lys Gly Gln Pro Arg Glu
            370                 375                 380

Pro Gln Val Tyr Thr Leu Pro Pro Ser Gln Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Arg
            435                 440                 445

Leu Thr Val Asp Lys Ser Arg Trp Gln Glu Gly Asn Val Phe Ser Cys
450                 455                 460

Ser Val Met His Glu Ala Leu His Asn His Tyr Thr Gln Lys Ser Leu
465                 470                 475                 480

Ser Leu Ser Leu Gly Lys Met Ala Leu Ile Val Leu Gly Gly Val Ala
                485                 490                 495

Gly Leu Leu Leu Phe Ile Gly Leu Gly Ile Phe Phe Lys Arg Gly Arg
            500                 505                 510

Lys Lys Leu Leu Tyr Ile Phe Lys Gln Pro Phe Met Arg Pro Val Gln
            515                 520                 525

Thr Thr Gln Glu Glu Asp Gly Cys Ser Cys Arg Phe Pro Glu Glu Glu
            530                 535                 540

Glu Gly Gly Cys Glu Leu Gly Gly Gly Arg Val Lys Phe Ser Arg Ser
545                 550                 555                 560

Ala Asp Ala Pro Ala Tyr Gln Gln Gly Gln Asn Gln Leu Tyr Asn Glu
                565                 570                 575

Leu Asn Leu Gly Arg Arg Glu Glu Tyr Asp Val Leu Asp Lys Arg Arg
            580                 585                 590

Gly Arg Asp Pro Glu Met Gly Gly Lys Pro Arg Arg Lys Asn Pro Gln
            595                 600                 605

Glu Gly Leu Tyr Asn Glu Leu Gln Lys Asp Lys Met Ala Glu Ala Tyr
            610                 615                 620

Ser Glu Ile Gly Met Lys Gly Glu Arg Arg Arg Gly Lys Gly His Asp
625                 630                 635                 640

Gly Leu Tyr Gln Gly Leu Ser Thr Ala Thr Lys Asp Thr Tyr Asp Ala
                645                 650                 655

Leu His Met Gln Ala Leu Pro Pro Arg Leu Glu Gly Gly Gly Glu Gly
            660                 665                 670

Arg Gly Ser Leu Leu Thr Cys Gly Asp Val Glu Glu Asn Pro Gly Pro
```

```
              675                 680                 685
Arg Met Leu Leu Leu Val Thr Ser Leu Leu Cys Glu Leu Pro His
    690                 695                 700

Pro Ala Phe Leu Leu Ile Pro Arg Lys Val Cys Asn Gly Ile Gly Ile
705                 710                 715                 720

Gly Glu Phe Lys Asp Ser Leu Ser Ile Asn Ala Thr Asn Ile Lys His
                725                 730                 735

Phe Lys Asn Cys Thr Ser Ile Ser Gly Asp Leu His Ile Leu Pro Val
            740                 745                 750

Ala Phe Arg Gly Asp Ser Phe Thr His Thr Pro Pro Leu Asp Pro Gln
        755                 760                 765

Glu Leu Asp Ile Leu Lys Thr Val Lys Glu Ile Thr Gly Phe Leu Leu
    770                 775                 780

Ile Gln Ala Trp Pro Glu Asn Arg Thr Asp Leu His Ala Phe Glu Asn
785                 790                 795                 800

Leu Glu Ile Ile Arg Gly Arg Thr Lys Gln His Gly Gln Phe Ser Leu
                805                 810                 815

Ala Val Val Ser Leu Asn Ile Thr Ser Leu Gly Leu Arg Ser Leu Lys
            820                 825                 830

Glu Ile Ser Asp Gly Asp Val Ile Ile Ser Gly Asn Lys Asn Leu Cys
        835                 840                 845

Tyr Ala Asn Thr Ile Asn Trp Lys Lys Leu Phe Gly Thr Ser Gly Gln
    850                 855                 860

Lys Thr Lys Ile Ile Ser Asn Arg Gly Glu Asn Ser Cys Lys Ala Thr
865                 870                 875                 880

Gly Gln Val Cys His Ala Leu Cys Ser Pro Glu Gly Cys Trp Gly Pro
                885                 890                 895

Glu Pro Arg Asp Cys Val Ser Cys Arg Asn Val Ser Arg Gly Arg Glu
            900                 905                 910

Cys Val Asp Lys Cys Asn Leu Leu Glu Gly Glu Pro Arg Glu Phe Val
        915                 920                 925

Glu Asn Ser Glu Cys Ile Gln Cys His Pro Glu Cys Leu Pro Gln Ala
    930                 935                 940

Met Asn Ile Thr Cys Thr Gly Arg Gly Pro Asp Asn Cys Ile Gln Cys
945                 950                 955                 960

Ala His Tyr Ile Asp Gly Pro His Cys Val Lys Thr Cys Pro Ala Gly
                965                 970                 975

Val Met Gly Glu Asn Asn Thr Leu Val Trp Lys Tyr Ala Asp Ala Gly
            980                 985                 990

His Val Cys His Leu Cys His Pro Asn Cys Thr Tyr Gly Cys Thr Gly
        995                 1000                1005

Pro Gly Leu Glu Gly Cys Pro Thr Asn Gly Pro Lys Ile Pro Ser
    1010                1015                1020

Ile Ala Thr Gly Met Val Gly Ala Leu Leu Leu Leu Val Val
    1025                1030                1035

Ala Leu Gly Ile Gly Leu Phe Met
    1040                1045

<210> SEQ ID NO 32
<211> LENGTH: 447
<212> TYPE: PRT
<213> ORGANISM: Artificial Sequence
<220> FEATURE:
<223> OTHER INFORMATION: Chimeric antigen receptor
```

<400> SEQUENCE: 32

```
Thr Asp Phe Thr Leu Thr Ile Ser Ser Leu Glu Pro Glu Asp Phe Ala
1               5                   10                  15

Val Tyr Tyr Cys Leu Gln Trp Ser Ser Asn Pro Leu Thr Phe Gly Gly
            20                  25                  30

Gly Thr Lys Val Glu Ile Lys Glu Ser Lys Tyr Gly Pro Pro Cys Pro
        35                  40                  45

Pro Cys Pro Ala Pro Glu Phe Glu Gly Gly Pro Ser Val Phe Leu Phe
    50                  55                  60

Pro Pro Lys Pro Lys Asp Thr Leu Met Ile Ser Arg Thr Pro Glu Val
65              70                  75                  80

Thr Cys Val Val Val Asp Val Ser Gln Glu Asp Pro Glu Val Gln Phe
            85                  90                  95

Asn Trp Tyr Val Asp Gly Val Glu Val His Asn Ala Lys Thr Lys Pro
            100                 105                 110

Arg Glu Glu Gln Phe Asn Ser Thr Tyr Arg Val Val Ser Val Leu Thr
        115                 120                 125

Val Leu His Gln Asp Trp Leu Asn Gly Lys Glu Tyr Lys Cys Lys Val
    130                 135                 140

Ser Asn Lys Gly Leu Pro Ser Ser Ile Glu Lys Thr Ile Ser Lys Ala
145                 150                 155                 160

Lys Gly Gln Pro Arg Glu Pro Gln Val Tyr Thr Leu Pro Pro Ser Gln
            165                 170                 175

Glu Glu Met Thr Lys Asn Gln Val Ser Leu Thr Cys Leu Val Lys Gly
        180                 185                 190

Phe Tyr Pro Ser Asp Ile Ala Val Glu Trp Glu Ser Asn Gly Gln Pro
    195                 200                 205

Glu Asn Asn Tyr Lys Thr Thr Pro Pro Val Leu Asp Ser Asp Gly Ser
    210                 215                 220

Phe Phe Leu Tyr Ser Arg Leu Thr Val Asp Lys Ser Arg Trp Gln Glu
225                 230                 235                 240

Gly Asn Val Phe Ser Cys Ser Val Met His Glu Ala Leu His Asn His
            245                 250                 255

Tyr Thr Gln Lys Ser Leu Ser Leu Ser Leu Gly Lys Met Ala Leu Ile
        260                 265                 270

Val Leu Gly Gly Val Ala Gly Leu Leu Leu Phe Ile Gly Leu Gly Ile
    275                 280                 285

Phe Phe Lys Arg Gly Arg Lys Lys Leu Leu Tyr Ile Phe Lys Gln Pro
290                 295                 300

Phe Met Arg Pro Val Gln Thr Thr Gln Glu Glu Asp Gly Cys Ser Cys
305                 310                 315                 320

Arg Phe Pro Glu Glu Glu Glu Gly Gly Cys Glu Leu Gly Gly Gly Arg
            325                 330                 335

Val Lys Phe Ser Arg Ser Ala Asp Ala Pro Ala Tyr Gln Gln Gly Gln
        340                 345                 350

Asn Gln Leu Tyr Asn Glu Leu Asn Leu Gly Arg Arg Glu Glu Tyr Asp
    355                 360                 365

Val Leu Asp Lys Arg Arg Gly Arg Asp Pro Glu Met Gly Gly Lys Pro
    370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
            405                 410                 415
```

Arg Gly Lys Gly His Asp Gly Leu Tyr Gln Gly Leu Ser Thr Ala Thr
        420                 425                 430

Lys Asp Thr Tyr Asp Ala Leu His Met Gln Ala Leu Pro Pro Arg
        435                 440                 445

<210> SEQ ID NO 33
<211> LENGTH: 114
<212> TYPE: PRT
<213> ORGANISM: Artificial Sequence
<220> FEATURE:
<223> OTHER INFORMATION: VL

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Leu Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Leu Asp Tyr Trp Gly Arg Gly Thr Leu Val Thr Val
            100                 105                 110

Ser Ser

<210> SEQ ID NO 34
<211> LENGTH: 107
<212> TYPE: PRT
<213> ORGANISM: Artificial Sequence
<220> FEATURE:
<223> OTHER INFORMATION: VH

<400> SEQUENCE: 34

Ser Glu Ile Val Leu Thr Gln Ser Pro Ala Thr Leu Ser Leu Ser Pro
1               5                   10                  15

Gly Glu Arg Ala Thr Leu Ser Cys Ser Ala Ser Ser Ile Asn Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Leu Gln Trp Ser Ser Asn Pro Leu
                85                  90                  95

Thr Phe Gly Gly Gly Thr Lys Val Glu Ile Lys
            100                 105

<210> SEQ ID NO 35
<211> LENGTH: 18
<212> TYPE: PRT
<213> ORGANISM: Artificial Sequence
<220> FEATURE:
<223> OTHER INFORMATION: spacer -continued

<400> SEQUENCE: 35

Gly Ser Thr Ser Gly Ser Lys Gly Pro Leu Gly Leu Ala Gly Ala Thr
1               5                   10                  15

Lys Gly

<210> SEQ ID NO 36
<211> LENGTH: 18
<212> TYPE: PRT
<213> ORGANISM: Artificial Sequence
<220> FEATURE:
<223> OTHER INFORMATION: spacer

<400> SEQUENCE: 36

Gly Ser Thr Ser Gly Ser Lys Gly Pro Lys Gly Leu Lys Gly Ala Thr
1               5                   10                  15

Lys Gly

<210> SEQ ID NO 37
<211> LENGTH: 14
<212> TYPE: PRT
<213> ORGANISM: Artificial Sequence
<220> FEATURE:
<223> OTHER INFORMATION: spacer

<400> SEQUENCE: 37

Gly Gly Gly Gly Ser Gly Gly Gly Ser Gly Gly Gly Gly
1               5                   10

<210> SEQ ID NO 38
<211> LENGTH: 234
<212> TYPE: PRT
<213> ORGANISM: Artificial Sequence
<220> FEATURE:
<223> OTHER INFORMATION: scFv

<400> SEQUENCE: 38

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Leu Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Leu Asp Tyr Trp Gly Arg Gly Thr Leu Val Thr Val
            100                 105                 110

Ser Ser Gly Ser Thr Ser Leu Gly Leu Ala Gly Ala Thr Lys Gly Ser
        115                 120                 125

Glu Ile Val Leu Thr Gln Ser Pro Ala Thr Leu Ser Leu Ser Pro Gly
    130                 135                 140

Glu Arg Ala Thr Leu Ser Cys Ser Ala Ser Ser Ile Asn Tyr Ile
145                 150                 155                 160

Tyr Trp Tyr Gln Gln Lys Pro Gly Gln Ala Pro Arg Leu Leu Ile Tyr
                165                 170                 175

Leu Thr Ser Asn Leu Ala Ser Gly Val Pro Ala Arg Phe Ser Gly Ser

```
                    180               185               190
Gly Ser Gly Thr Asp Phe Thr Leu Thr Ile Ser Ser Leu Glu Pro Glu
            195               200               205

Asp Phe Ala Val Tyr Tyr Cys Leu Gln Trp Ser Ser Asn Pro Leu Thr
        210               215               220

Phe Gly Gly Gly Thr Lys Val Glu Ile Lys
225             230

<210> SEQ ID NO 39
<211> LENGTH: 239
<212> TYPE: PRT
<213> ORGANISM: Artificial Sequence
<220> FEATURE:
<223> OTHER INFORMATION: scFv

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Leu Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Leu Asp Tyr Trp Gly Arg Gly Thr Leu Val Thr Val
            100                 105                 110

Ser Ser Gly Ser Thr Ser Gly Ser Gly Lys Pro Gly Ser Gly Glu Gly
        115                 120                 125

Ser Thr Lys Gly Ser Glu Ile Val Leu Thr Gln Ser Pro Ala Thr Leu
    130                 135                 140

Ser Leu Ser Pro Gly Glu Arg Ala Thr Leu Ser Cys Ser Ala Ser Ser
145                 150                 155                 160

Ser Ile Asn Tyr Ile Tyr Trp Tyr Gln Gln Lys Pro Gly Gln Ala Pro
                165                 170                 175

Arg Leu Leu Ile Tyr Leu Thr Ser Asn Leu Ala Ser Gly Val Pro Ala
            180                 185                 190

Arg Phe Ser Gly Ser Gly Ser Gly Thr Asp Phe Thr Leu Thr Ile Ser
        195                 200                 205

Ser Leu Glu Pro Glu Asp Phe Ala Val Tyr Tyr Cys Leu Gln Trp Ser
    210                 215                 220

Ser Asn Pro Leu Thr Phe Gly Gly Gly Thr Lys Val Glu Ile Lys
225                 230                 235
```